(12) United States Patent
Long

(10) Patent No.: US 11,679,173 B2
(45) Date of Patent: Jun. 20, 2023

(54) PORTABLE SANITIZER SPRITZIER SYSTEM

(71) Applicant: Traci Long, Kissimmee, FL (US)

(72) Inventor: Traci Long, Kissimmee, FL (US)

( * ) Notice: Subject to any disclaimer, the term of this patent is extended or adjusted under 35 U.S.C. 154(b) by 287 days.

(21) Appl. No.: 17/193,740

(22) Filed: Mar. 5, 2021

(65) Prior Publication Data

US 2022/0280670 A1    Sep. 8, 2022

(51) Int. Cl.
*A61L 2/22* (2006.01)
*A61L 2/26* (2006.01)
*A61L 2/07* (2006.01)

(52) U.S. Cl.
CPC ............. *A61L 2/22* (2013.01); *A61L 2/07* (2013.01); *A61L 2/26* (2013.01); *A61L 2202/14* (2013.01); *A61L 2202/15* (2013.01); *A61L 2202/16* (2013.01); *A61L 2202/20* (2013.01)

(58) Field of Classification Search
CPC .......... A61L 2/22; A61L 2/07; A61L 2202/15; A61L 2/26; A61L 2202/16
See application file for complete search history.

(56) References Cited

U.S. PATENT DOCUMENTS

| | | | | |
|---|---|---|---|---|
| 10,894,106 B1 * | 1/2021 | Lopez | ........... | A47F 10/04 |
| 2005/0214159 A1 * | 9/2005 | Schwei | ........... | A61L 2/24 |
| | | | | 422/28 |
| 2006/0011220 A1 * | 1/2006 | Mueller | ........... | B08B 3/022 |
| | | | | 134/123 |
| 2006/0117590 A1 * | 6/2006 | Swisher | ........... | F26B 21/004 |
| | | | | 34/216 |
| 2007/0084650 A1 * | 4/2007 | Schwei | ........... | B08B 3/02 |
| | | | | 422/1 |
| 2008/0029133 A1 * | 2/2008 | Kunkle | ........... | A61L 2/22 |
| | | | | 134/123 |
| 2008/0178412 A1 * | 7/2008 | Kiter | ........... | A61L 2/10 |
| | | | | 15/4 |
| 2012/0045365 A1 * | 2/2012 | Lee | ........... | A61L 2/07 |
| | | | | 422/292 |
| 2013/0087176 A1 * | 4/2013 | Sappington | ........... | B08B 9/28 |
| | | | | 134/123 |
| 2015/0052675 A1 * | 2/2015 | Desmelyk | ........... | A47K 3/28 |
| | | | | 4/597 |
| 2018/0326950 A1 * | 11/2018 | Sturgill | ........... | B08B 3/022 |
| 2020/0306395 A1 * | 10/2020 | Gardiner | ........... | A61L 2/10 |

* cited by examiner

*Primary Examiner* — Maris R Kessel
*Assistant Examiner* — Justin Hwang
(74) *Attorney, Agent, or Firm* — Lyman Moulton, Esq.; Moulton Patents, PLLC

(57) ABSTRACT

The Portable Sanitizer Spritzier Station as disclosed includes an undercarriage of frontward and backward motion rollers and sidewards rollers configured to ambulate the station in a first mode and to convey carts there through in a second mode and to collect used sanitizer for recycle and refuse. The disclosure also includes an upper structure of clear side panels and clear tarp ends and inside guide rails between conveyor belts and a sanitizer pipe network directing sanitizer upward from a floor thereof and downward from a ceiling thereof. The disclosure further includes a controller configured to determine one of the first and the second modes and to determine a time limit for the sanitizer to be sprayed through the sanitizer pipes and to control the rollers and conveyor belt.

19 Claims, 1 Drawing Sheet

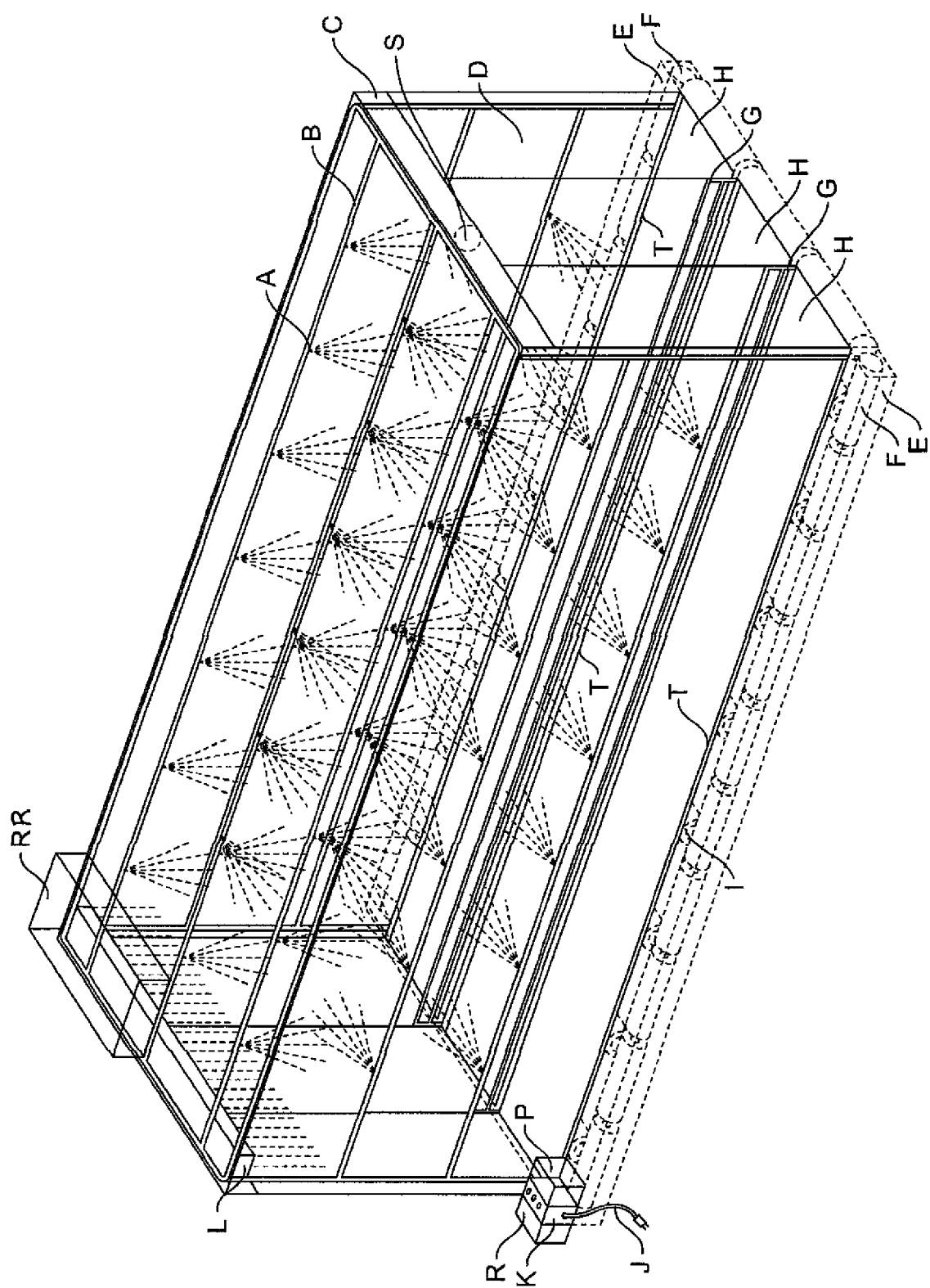

PORTABLE SANITIZER SPRITZIER SYSTEM

BACKGROUND

In modern time, cleansing the surface of a commonly used object is an essential procedure, in order to prevent the spread of diseases. However, for businesses within the retail industry, sanitizing the surfaces of shopping carts, baskets, and wheelchairs, is an extensive process that demands large volumes of manual labor to ensure proper execution and public safety, especially in unique times of a COVID pandemic. There have been no products available as original equipment or as an aftermarket to address this problem.

An apparatus or system is to simplify the process of sanitizing shopping carts, wheelchairs, baskets and other commonly used objects. A system, that limits the amount of manpower and manual labor. There have been no products available as original equipment or as an aftermarket to address this problem either. There exists a need for a device and a system that is not being met by any known or disclosed device or system of present.

SUMMARY OF THE INVENTION

The main purpose of the Portable Sanitizer Spritzier Station is to provide an efficient and prompt system of thoroughly sanitizing mobile vessels, specifically, shopping carts and wheelchairs. The Portable Sanitizer Spritzier Station is designed to alleviate the burden of hand-cleaning individual shopping carriers by sanitizing numerous items at once.

A sanitizing station as disclosed includes an undercarriage of frontward and backward motion rollers and sidewards rollers configured to ambulate the station in a first mode and to convey carts there through in a second mode and to collect used sanitizer for recycle and refuse. The disclosure also includes an upper structure of clear side panels and clear tarp ends and inside guide rails between conveyor belts and a sanitizer pipe network directing sanitizer upward from a floor thereof and downward from a ceiling thereof. The disclosure further includes a controller configured to determine one of the first and the second modes and to determine a time limit for the sanitizer to be sprayed through the sanitizer pipes and to control the rollers and conveyor belts.

The sanitizer station further comprising a pump controlled by the controller to create a positive pressure for spraying the sanitizer through the pipe network, and a reservoir of sanitizing solution disposed above the station for a gravity feed of the sanitizer through the pipe network.

The sanitizer station wherein the clear side panels comprise plexiglass and the clear tarp ends comprise a low durometer clear plastic composite.

The sanitizer station wherein the inside guide rails between conveyor belts are one of two guide rails configured to retain a shopping cart traveling on one of three conveyor belts.

The sanitizer station further comprising an air curtain blow dryer disposed at an exit end of the station.

The sanitizer station wherein the sanitizer pipe network comprises ceiling pipes directing sanitizer downward, floor pipes directing sanitizer upward and lateral pipes directing sanitizer laterally onto a shopping cart.

The sanitizer station wherein the first mode ambulates the sanitizer station forwards and backwards via the frontward and the backward motion rollers based on the sideways rollers rescinded into the undercarriage. Wherein the first mode ambulates the sanitizer station sideways via the sideways rollers based on the frontward and backward rollers rescinded into the undercarriage.

The sanitizer station wherein the second mode conveys carts there through via the frontward and the backward motion rollers which are recessed upward into the upper structure in contact with the carts based on the sideways rollers being stationary on the undercarriage in contact with a ground surface.

The sanitizer station wherein the controller takes input from a user who determines an operation of the sanitizer station in the first mode or in the second mode.

The sanitizer station wherein the controller determines the time limit from a user input and an electronic timer and a mechanical timer.

The sanitizer station wherein the controller determines a speed of conveyor belt movement based on determining a speed of the backward and the forward rollers from a user input.

The sanitizer station wherein the controller determines an amount of sanitizer to be sprayed from the sanitizer pipes via a plurality of nozzles and an input from a user.

The sanitizer station, wherein the undercarriage collects used sanitizer for recycle and refuse via a plurality of lateral troughs and a catch basin in the undercarriage.

The sanitizer station wherein the controller comprises a wireless transceiver circuitry for communicating remotely with a user.

The sanitizer station further comprising a reservoir for mixing sanitizer compounds and for sourcing sanitizer to the pipe network.

The sanitizer station further comprising clear ceiling panels, clear side panels and clear tarp ends to enclose a space within the upper structure for sanitizing via steam applications through the piping network.

The sanitizer station further comprising a heater configured to heat the sanitizer for steam applications.

The sanitizer station further comprising a thermostat inside the upper structure and in communication with the controller to maintain a sterilizing heat within the upper structure via a heater.

BRIEF DESCRIPTION OF THE DRAWINGS

FIG. 1. This is a perspective view of the Portable Sanitizer Spritzier Station in accordance with an embodiment of the present disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

Throughout the present disclosure, the term spritzier and 'spray' are used interchangeably.

FIG. 1. This is a perspective view of the Portable Sanitizer Spritzier Station in accordance with an embodiment of the disclosure. The view shows: A. Sanitizing spray, B. Pipe structure carrying sanitizer, C. Plexiglass structure, D. Clear plastic tarp panels, E. Locked cylinder box, F. Cylinders, G. Metal guide rail, H. Conveyor belt, I. Rollers, J. Power cord, K. Control box (Timer set, turn on/off conveyor), and L. Air curtain blow dryer, in accordance with an embodiment of the present disclosure. The view also includes a pump P, a heater R, drain troughs T, a sanitizer reservoir RR and a thermostat S as depicted.

The Portable Sanitizer Spritzier Station features a rectangular shape and is constructed from reliable plexiglass, granting an inclusive view of the sanitization process. A durable plastic tarp panel is positioned above the entrance and exit section of the system, providing a simple yet protected access to objects of various sizes managed within. The product is comprised of pipes carrying disinfectant fluids and sprayers to effectively project the cleaning material onto the objects in an effective and liberal manner, covering all exposed areas. The Portable Sanitizer Spritzier Station is also equipped with a guide rail constructed from high-quality metal to secure placement of the items funneled through the unit. Three novel conveyor belts line the Portable Sanitizer Spritzer Station, supporting the decontamination of several items at once, with the conveyor belts powered by sturdy cylinders and rollers to ensure a leveled and uninterrupted transition. Furthermore, the Portable Sanitizer Spritzier Station can be programmed to operate for a set amount of time via the control box. The Portable Sanitizer Spritzier Station helps in preventing disease transmission and increasing customer satisfaction.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

What is claimed is:

1. A sanitizing station comprising:
    an undercarriage of frontward and backward motion rollers and sideways rollers configured to ambulate the station in a first mode and to convey carts there through in a second mode and to collect used sanitizer for recycle and refuse;
    an upper structure of clear side panels and clear tarp ends and inside guide rails between conveyor belts and a sanitizer pipe network directing sanitizer upward from a floor thereof and downward from a ceiling thereof, wherein the second mode conveys carts there through via the frontward and the backward motion rollers which are recessed upward into the upper structure in contact with the carts based on the sideways rollers being stationary on the undercarriage in contact with a ground surface; and
    a controller configured to determine one of the first and the second modes and to determine a time limit for the sanitizer to be sprayed from the sanitizer pipes and to control the frontward, backward, and sideways rollers and conveyor belts.

2. The sanitizer station of claim 1, further comprising a pump controlled by the controller to create a positive pressure for spraying the sanitizer through the pipe network.

3. The sanitizer station of claim 1, further comprising a reservoir of sanitizing solution disposed above the station for a gravity feed of the sanitizer through the pipe network.

4. The sanitizer station of claim 1, wherein the clear side panels comprise plexiglass and the clear tarp ends comprise a low durometer clear plastic composite.

5. The sanitizer station of claim 1, wherein the inside guide rails between conveyor belts are one of two guide rails configured to retain a shopping cart traveling on one of three conveyor belts.

6. The sanitizer station of claim 1, further comprising an air curtain blow dryer disposed at an exit end of the station.

7. The sanitizer station of claim 1, wherein the sanitizer pipe network comprises ceiling pipes directing sanitizer downward, floor pipes directing sanitizer upward and lateral pipes directing sanitizer laterally onto a shopping cart.

8. The sanitizer station of claim 1, wherein the first mode ambulates the sanitizer station forwards and backwards via the frontward and the backward motion rollers based on the sideways rollers rescinded into the undercarriage.

9. The sanitizer station of claim 1, wherein the first mode ambulates the sanitizer station sideways via the sideways rollers based on the frontward and backward rollers rescinded into the undercarriage.

10. The sanitizer station of claim 1, wherein the controller takes input from a user who determines an operation of the sanitizer station in the first mode or in the second mode.

11. The sanitizer station of claim 1, wherein the controller determines the time limit from a user input and an electronic timer and a mechanical timer.

12. The sanitizer station of claim 1, wherein the controller determines a speed of conveyor belt movement based on determining a speed of the backward and the forward rollers from a user input.

13. The sanitizer station of claim 1, wherein the controller determines an amount of sanitizer to be sprayed from the sanitizer pipes via a plurality of nozzles and an input from a user.

14. The sanitizer station of claim 1, wherein the undercarriage collects used sanitizer for recycle and refuse via a plurality of lateral troughs and a catch basin in the undercarriage.

15. The sanitizer station of claim 1, wherein the controller comprises a wireless transceiver circuitry for communicating remotely with a user.

16. The sanitizer station of claim 1, further comprising a reservoir for mixing sanitizer compounds and for sourcing sanitizer to the pipe network.

17. The sanitizer station of claim 1, further comprising clear ceiling panels, clear side panels and clear tarp ends to enclose a space within the upper structure for sanitizing via steam applications through the piping network.

18. The sanitizer station of claim 1, further comprising a heater configured to heat the sanitizer for steam applications.

19. The sanitizer station of claim 1, further comprising a thermostat inside the upper structure and in communication with the controller to maintain a sterilizing heat within the upper structure via a heater.

* * * * *